US007211658B2

(12) United States Patent
Herrmann et al.

(10) Patent No.: US 7,211,658 B2
(45) Date of Patent: May 1, 2007

(54) INSECTICIDAL PLANT CYCLOTIDE WITH ACTIVITY AGAINST HOMOPTERAN INSECTS

(75) Inventors: Rafael Herrmann, Wilmington, DE (US); Albert L. Lu, Newark, DE (US); Billy F. McCutchen, Clive, IA (US); James K. Presnail, Avondale, PA (US); Janet A. Rice, Wilmington, DE (US); Clement W. K. Waine, Newark, DE (US)

(73) Assignee: E.I. duPont deNemours and Company, Wilmington, DE (US)

( * ) Notice: Subject to any disclaimer, the term of this patent is extended or adjusted under 35 U.S.C. 154(b) by 0 days.

(21) Appl. No.: 11/236,922

(22) Filed: Sep. 28, 2005

(65) Prior Publication Data

US 2006/0236423 A1    Oct. 19, 2006

Related U.S. Application Data

(60) Provisional application No. 60/616,190, filed on Oct. 5, 2004.

(51) Int. Cl.
*C12N 15/29* (2006.01)
*C12N 15/82* (2006.01)

(52) U.S. Cl. .................................. 536/23.6; 435/320.1
(58) Field of Classification Search ...................... None
See application file for complete search history.

(56) References Cited

U.S. PATENT DOCUMENTS

2003/0158096 A1    8/2003    Craik et al.

FOREIGN PATENT DOCUMENTS

| WO | WO 01/27147    | 4/2001  |
| WO | WO 01/34829    | 5/2001  |
| WO | WO 2004/055044 | 7/2004  |
| WO | WO 2005/108596 | 11/2005 |

OTHER PUBLICATIONS

Craik et al. 1999, J. Mol. Biol. 294:1327-1336.*
Craik et al. 2001, GenBank Accession No. P58439.*
Witherup, et al., Cyclopsychotride A, A Biologically Active, 31-Residue Cyclic Peptide Isolated from Psychotria Longpipes, J. Nat. Prod., (1994), 57(12): 1619-1625.
Claeson, et al., fractionation Protocol for the Isolation of Polypeptides from Plant Biomass, J. Nat. prod., (1998), 61: 77-81.
Tam, et al., A biomimetic strategy in the synthesis and fragmentation of cyclic protein, Protein Science, (1998), 7:1583-1592.
Tam, et al., Thia Zip Reaction for Synthesis of Large Cyclic Peptides: mechanisms and Applications, J. Am. Chem. Soc., (1999), 121:4316-4324.
Tam, et al., An unusual structural motif of antimicrobial peptides containing end-to-end macrocycle and cystine-knot disulfides, Proc. Natl. Acad. Sci. USA, (1999), 96:8913-8918.
Daly, et al., Solution Structure by NMR of Circulin A: A Macrocyclic Knotted Peptide Having Anti-HIV Activity, J. Mol. Biol., (1999), 285:333-345.
Craik, et al., Plant Cyclotides: A Unique Family of Cyclic and Knotted Proteins that Defines the Cyclic Cystine Knot Structural Motif, J. Mol. Biol (1999), 294: 1327-1336.
Goransson, et al., Seven Novel Macrocyclic Polypeptides from *Viola arvensis*, J. Nat. Prod. (1999), 62: 283-286.
Daly, et al., Chemical Synthesis and Folding Pathways of Large Cyclic polypeptides: Studies of the Cystine Knot Polypeptide Kalata B1, Biochemistry (1999), 38: 10606-10614.
Hallock, et al., Cycloviolins A-D Anti-HIV Macrocyclic peptides from *Leonia cymosa*, J. Org. Chem., (2000), 65:124-128.
Hernandez, et al., Squash Trypsin Inhibitors from *Momordica cochinchinensis* Exhibit an Atypical Macrocyclic Structure, Biochem., (2000), 39:5722-5730.
Gran, et al., A plant containing uteroactive peptides used in African traditional medicine, J. of Ethnopharmacology, (2000), 70: 197-203.
Gustafson, et al., New Circulin Macrocyclic Polypeptides from *Chassalia parvifolia*, J. Nat. Prod. (2000), 63: 176-178.
Daly, et al., Acyclic Permutants of Naturally Occuring Cyclic Proteins, J. Biol. Chem. (2000), 275(25): 19068-19075.
Craik, et al., The cystine knot motif in toxins and implications for drug design, Toxicon, (2001), 39: 43-60.
Heitz, et al., Solution Structure of the Squash Trypsin Inhibitor MCoTI-II. A New Family for Cyclic Knottins, Biochem., (2001), 40:7973-7983.
Bokesch, et al., A Novel Anti-HIV Macrocyclic Peptide from *Palicourea condensate*, J. Nat. Prod., (2001), 64:249-250.
Craik, David J., Plant cyclotides: circular, knotted peptide toxins, Toxicon (2001), 39: 1809-1813.
Felizmenio-Quimio, et al., Circular Proteins in Plants, J. Biol. Chem. (2001), 276(25): 22875-22882.
Broussalis, et al., First Cyclotide from *Hybanthus*, (Violaceae), Phytochemistry (2001), 58: 47-51.
Jennings, et al., Biosynthesis and insecticidal properties of plant cyclotides: The cyclic knotted proteins from *Oldenlandia affinis*, PNAS (2001), 98(19): 10614-10619.
Skjeldal, et al., Refined Structure and Metal Binding Site of the Kalata B1 Peptide, Biochem. Biophys., (2002), 399(2): 142-148.
Craik, et al., The cyclotides: Novel macrocyclic peptides as scaffolds in drug design, Current Opinion in Drug Discovery & Development, (2002), 5(2): 251-260.
Trabi, et al., Circular proteins—no end in sight, Trends Biochem. Sci. (2002), 27(3): 132-138.
Barry, et al., Linearization of a Naturally Occurring Circular Protein Maintains Structure but Eliminates Hemolytic Activity, Biochem., (2003), 42:6688-6695.
Goransson, et al., Expression of Viola cyclotides by liquid chromatography-mass spectrometry and tandem mass, spectrometry sequencing of intercysteine loops after introduction of charges and cleavage sites by aminoethylation, Analytical Biochemistry, (2003), 318:107-117.

(Continued)

*Primary Examiner*—Elizabeth Mcelwain
*Assistant Examiner*—Li Zheng

(57) ABSTRACT

The present invention relates to isolated nucleic acids encoding plant cyclotides. The invention also relates to the construction of a chimeric gene encoding all or a portion of the plant cyclotides, in sense or antisense orientation, wherein expression of the chimeric gene results in the production of altered levels of plant cyclotides in a transformed host cell.

4 Claims, 1 Drawing Sheet

OTHER PUBLICATIONS

Daly, et al., Disulfide Folding Pathways of Cystine Knot Proteins, J. Biol. Chemistry, (2003), 278(8):6314-6322.

Goransson, et al., Disulfide Mapping of the Cyclotide Kalata B1, J. of Biol. Chemistry, (2003), 278(48):48188-48196.

Craik, et al., Structure-Function Studies of the Plant Cyclotides: The Role of a Circular Protein Backbone, J. Toxicol. Toxin Rev. (2003), 22: 555-576.

Rosengren, et al., Twists, Knots, and Rings in Proteins, J. Biol. Chem. (2003), 278(10): 8606-8616.

Svangard, et al., Primary and 3-D modeled structures of two cyclotides from *Viola odorata*, Phytochemistry (2003), 64: 135-142.

Goransson, et al., Reversible Antifouling Effect of the Cyclotide cycloviolacin O2 against Barnacles, J. nat. Prod., (2004), 67: 1287-1290.

Barry, et al., Solution Structure of the Cyclotide Palicourein: Implications for the Development of a Pharmaceutical Framework, Structure, (2004), 12: 85-94.

Trabi, et al., Tissue-Specific Expression of Head-to-Tail Cyclized Miniproteins in Violaceae and Structure Determination of the root cyclotide *Viola hederacea* root cyclotide1, Plant Cell (2004), 16: 2204-2216.

Craik, et al., Discovery, Structure and Biological Activities of the Cyclotides, Curr. Prot. Pept. Sci. (2004), 5:297-315.

Trabi, et al., Variations in Cyclotide Expression in *Viola* Species, J. Nat. Prod. (2004), 67: 806-810.

Svangard, et al., Cytotoxic Cyclotides from *Viola tricolor*, J. Nat. Prod. (2004), 67: 144-147.

Colgrave, et al., Thermal, Chemical, and Enzymatic Stability of the Cyclotide Kalata B1: The Importance of the Cyclic Cystine Knot, Biochemistry (2004), 43: 5965-5975.

Nourse, et al., A comparison of the Self-association Behavior of the Plant Cyclotides Kalata B1 and Kalata B2 via Analytical Ultracentrifugation, J. of Biol. Chemistry, (2004), 279(1):562-570.

Daly, et al., The role of the cyclic peptide backbone in the anti-HIV activity of the cyclotide kalata B1, FEBS Letters, (2004), 574:69-72.

NCBI (2003), Accession P58439.

NCBI (2003), Accession P58445.

Craik, DJ et al., Discovery and applications of the cyclotides: Circular proteins from plants, Biopolymers, (2003), 71(3) 281, XP009064601.

* cited by examiner

INSECTICIDAL PLANT CYCLOTIDE WITH ACTIVITY AGAINST HOMOPTERAN INSECTS

CROSS-REFERENCE TO RELATED APPLICATIONS

This application claims the benefit of U.S. Provisional Application Ser. No. 60/616,190, filed Oct. 5, 2004, the content of which is herein incorporated by reference in its entirety.

FIELD OF THE INVENTION

Embodiments of the present invention relate to naturally-occurring and recombinant nucleic acids encoding cyclotides characterized by activity against plant pathogens. Compositions and methods of certain embodiments of the invention utilize the disclosed nucleic acids, and their encoded polypeptides to control plant pathogens.

BACKGROUND OF THE INVENTION

Plant pathogens are responsible for significant annual crop yield losses. One strategy for the control of plant pathogens is the use of resistant cultivars selected for, or developed by, plant breeders for this purpose. However, novel mechanisms for pathogen resistance can be implemented more quickly by molecular methods of crop protection than by traditional breeding methods. Accordingly, molecular methods are needed to supplement traditional breeding methods to protect plants from pathogen attack.

Plants rely heavily on a chemical and biological armory for their defense from a variety of pests and pathogens. Small cysteine-rich proteins that have been implicated in host defense and isolated from plant sources include defensins, thionins, and small antimicrobial proteins (AMP's). Cyclotides, also cysteine-rich molecules, have recently been recognized and characterized as being involved in host defense (Craik et al. (1999), *J. Mol. Biol.* 294: 1327–1336; Craik et al. (2000), *Toxicon* 39: 43–60). Cyclotide polypeptides are encoded by gene sequences, are produced as linear precursors, are cysteine-rich, and are capable of being cyclized via a peptide bond. Cyclotides display a diverse range of biological activities such as antibacterial activity, antifungal activity, anti-HIV activity, and uterotonic activity (Craik (2001), *Toxicon* 39: 1809–1813). Cyclotides have additionally been shown to possess insecticidal activity (Jennings et al. (2001) *Proc. Natl. Acad. Sci. U.S.A.* 98:10614–10619). Cyclized cyclotides differ from classical proteins in that they have no free N- or C-terminus due to their amide-circularized backbone.

Cyclotide polypeptides are derived from longer precursor proteins and thus both cleavage and cyclization steps are involved in the production of the cyclic backbone. The cyclic backbone of the cyclotide molecule typically ranges in size from 29 to 37 amino acid residues and has three disulfide bonds that form a cystine knot motif where two disulfide bonds and their connecting backbone strands form a ring that is threaded by the third disulfide bond. The mechanism(s) inherent to backbone cyclization is currently not known. One possibility is enzymatic or chemical involvement in both the backbone cleavage of the mature domain and the subsequent cyclization. The combined features of the cyclic cystine knot produce a unique protein fold that is topologically complex and has exceptional chemical and biological stability.

The majority of the plant cyclotides have been isolated from Rubiaceae and Violaceae plants (Gustafson et al. (1994), *J. Nat. Prod.* 116: 9337–9338; Gustafson et al. (2000), *J. Nat. Prod.* 63: 176–178; Witherup et al. (1994), *J. Nat. Prod.* 57: 1619–1625; Saether et al. (1995), *Biochemistry* 34, 4147–4158; Bokesch et al. (2001), *J. Nat. Prod.* 64: 249–250; Schöpke et al. (1993), *Sci. Pharm.* 61: 145–153; Claeson et al. (1998), *J. Nat. Prod.* 61: 77–81; Göransson et al. (1999), *J. Nat. Prod.* 62: 283–286; Hallock et al. (2000), *J. Org. Chem.* 65: 124–128; Broussalis et al. (2001), *Phytochemistry* 58: 47–51). Recently, two members of a new sub-class of the cyclotide family have been discovered in Curcurbitaceae (Hernandez et al. (2000), *Biochemistry* 39: 5722–5730; Felizmenio-Quimio et al. (2001), *J. Biol. Chem.* 276: 22875–22882; Heitz et al. (2001), *Biochemistry* 40: 7973–7983; Trabi and Craik, (2002), *Trends in Biochem. Sci.* 27: 132–138).

Cyclotides may be used in transgenic plants in order to produce plants with increased resistance to pathogens such as fungi, viruses, bacteria, nematodes, and insects. Thus, embodiments of the present invention solve needs for the enhancement of a plant's defensive response via a molecularly based mechanism which can be quickly incorporated into commercial crops.

SUMMARY OF THE INVENTION

Compositions and methods relating to pathogen resistance are provided.

Embodiments of the invention include a cyclotide sequence which finds use in enhancing the plant pathogen defense system. Further embodiments include compositions and methods which can be used for enhancing plant resistance to Homopteran insect pests. The method involves stably transforming a plant with a nucleotide sequence capable of modulating the plant pathogen defense system operably linked with a promoter capable of driving expression of a gene in a plant cell.

Transformed plants, plant cells, and seeds, as well as methods for making such plants, plant cells, and seeds, are additionally provided. It is recognized that a variety of promoters will be useful in the various embodiments of the invention, the choice of which will depend in part upon the desired level of expression of the disclosed genes. It is recognized that the levels of expression can be controlled to modulate the levels of expression in the plant cell.

Embodiments of the invention are directed to a cyclizable molecule and its linear precursor; cyclic peptides, polypeptides or proteins; and additionally includes the linear forms of non-cyclic structural homologues of the cyclic peptides, polypeptides and proteins. Also included are derivative forms of the cyclized molecule and their linear precursors encoded by the subject nucleic acid molecules. The cyclic and linear peptides, polypeptides or proteins may be naturally occurring or may be modified by the insertion or substitution of heterologous amino acid sequences.

One embodiment of the invention provides an isolated nucleic acid molecule comprising a sequence of nucleotides, which sequence of nucleotides encodes an amino acid sequence or a derivative form thereof capable of being cyclized within a cell or a membrane of a cell to form a cyclic backbone wherein the cyclic backbone comprises sufficient disulfide bonds to confer a stabilized folded structure on the three dimensional structure of the backbone. The amino acid sequence may also be cyclizable in an in vitro system comprising, for example, cyclizing enzymes or a chemical means for cyclization.

Embodiments of the invention also extend to the peptide, polypeptide or protein sequences which are capable of cyclizing in the absence of any other exogenous factor and more specifically capable of circularizing through a catalytic process being an inherent activity of the peptides, polypeptides or proteins.

Embodiments of the invention comprise a peptide sequence that can be processed from a larger polypeptide sequence, more specifically, a peptide sequence which can be cleaved and cyclized. Such embodiments further extend to linear forms and precursor forms of the peptide, polypeptide or protein which may also have activity or other utilities. Other embodiments extend to engineering crop plants with the sequences of the invention in order to produce plants that are resistant to pathogens.

Embodiments of the invention concern an isolated polynucleotide comprising a nucleotide sequence set forth in SEQ ID NOs: 1, 4 or 5; a nucleotide sequence that encodes a polypeptide having the amino acid sequence set forth in SEQ ID NOs: 2, 3, or 6, a nucleotide sequence characterized by at least 85% sequence identity to the nucleotide sequences set forth in SEQ ID NOs: 1, 4 and 5; a nucleotide sequence characterized by at least 90% sequence identity to the nucleotide sequences set forth in SEQ ID NOs: 1, 4 and 5; a nucleotide sequence characterized by at least 95% sequence identity to the nucleotide sequences set forth in SEQ ID NOs: 1, 4 and 5; and a nucleotide sequence that comprises the complement of any one of the above. A further embodiment is the complement of the nucleotide sequences disclosed herein.

Embodiments of the invention also relate to a chimeric gene comprising an isolated polynucleotide of the present invention operably linked to suitable regulatory sequences.

A further embodiment of the invention concerns an isolated host cell comprising a chimeric gene or an isolated polynucleotide. The host cell may be eukaryotic, such as a yeast or a plant cell, or prokaryotic, such as a bacterial cell. Another embodiment relates to a virus, such as a baculovirus, comprising an isolated polynucleotide or a chimeric gene.

Another embodiment of the invention provides a process for producing an isolated host cell comprising a chimeric gene or an isolated polynucleotide, the process comprising either transforming or transfecting an isolated compatible host cell with a chimeric gene or isolated polynucleotide.

An embodiment of the invention also provides an isolated polypeptide selected from the group consisting of: a polypeptide comprising an amino acid sequence set forth in SEQ ID NOs: 2, 3 or 6; a polypeptide characterized by at least 90% identity to SEQ ID NOs: 2, 3 or 6; a polypeptide characterized by at least 95% identity to SEQ ID NOs: 2, 3 or 6; a polypeptide characterized by at least 97% identity to SEQ ID NOs: 2, 3 or 6; a polypeptide characterized by at least 98% identity to SEQ ID NOs: 2, 3 or 6; and a polypeptide characterized by at least 99% identity to SEQ ID NOs: 2, 3 or 6. The polypeptides are useful in protecting plants from various Homopteran insect pests including, but not limited to, corn plant hopper (*Peregrinus maidis*) and soybean aphid (*Aphis glycines*).

An embodiment additionally provides a method for impacting a plant Homopteran insect comprising introducing into a plant or cell thereof at least one nucleotide construct comprising a coding sequence operably linked to a promoter that drives expression of a plant cyclotide polypeptide in plant cells, wherein said nucleotide sequence is selected from the group consisting of: a nucleotide sequence set forth in SEQ ID NOs: 1, 4 or 5; a nucleotide sequence that encodes a polypeptide having the amino acid sequence set forth in SEQ ID NOs: 2, 3 or 6; a nucleotide sequence characterized by at least 85% sequence identity to the nucleotide sequences set forth in SEQ ID NOs: 1, 4 or 5; a nucleotide sequence characterized by at least 90% sequence identity to the nucleotide sequences set forth in SEQ ID NOs: 1, 4 or 5; a nucleotide sequence characterized by at least 95% sequence identity to the nucleotide sequences set forth in SEQ ID NOs: 1, 4 or 5; and a nucleotide sequence that comprises the complement of any one of the above.

Expression cassettes and stably transformed plants are also provided by embodiments of the invention. Other embodiments provide nucleic acids and fragments and variants thereof which encode polypeptides or mature polypeptides that possess activity against plant Homopteran pests.

In a particular embodiment, a transformed plant of the invention can be produced using a nucleic acid that has been optimized for increased expression in a host plant. For example, the cyclotide polypeptides can be back-translated to produce nucleic acids comprising codons optimized for expression in a particular host, for example a crop plant such as a soybean plant or a maize plant. Some embodiments provide transgenic plants expressing polypeptides that find use in methods for impacting plant Homopteran insect pests.

DETAILED DESCRIPTION OF THE INVENTION

Figure 1:
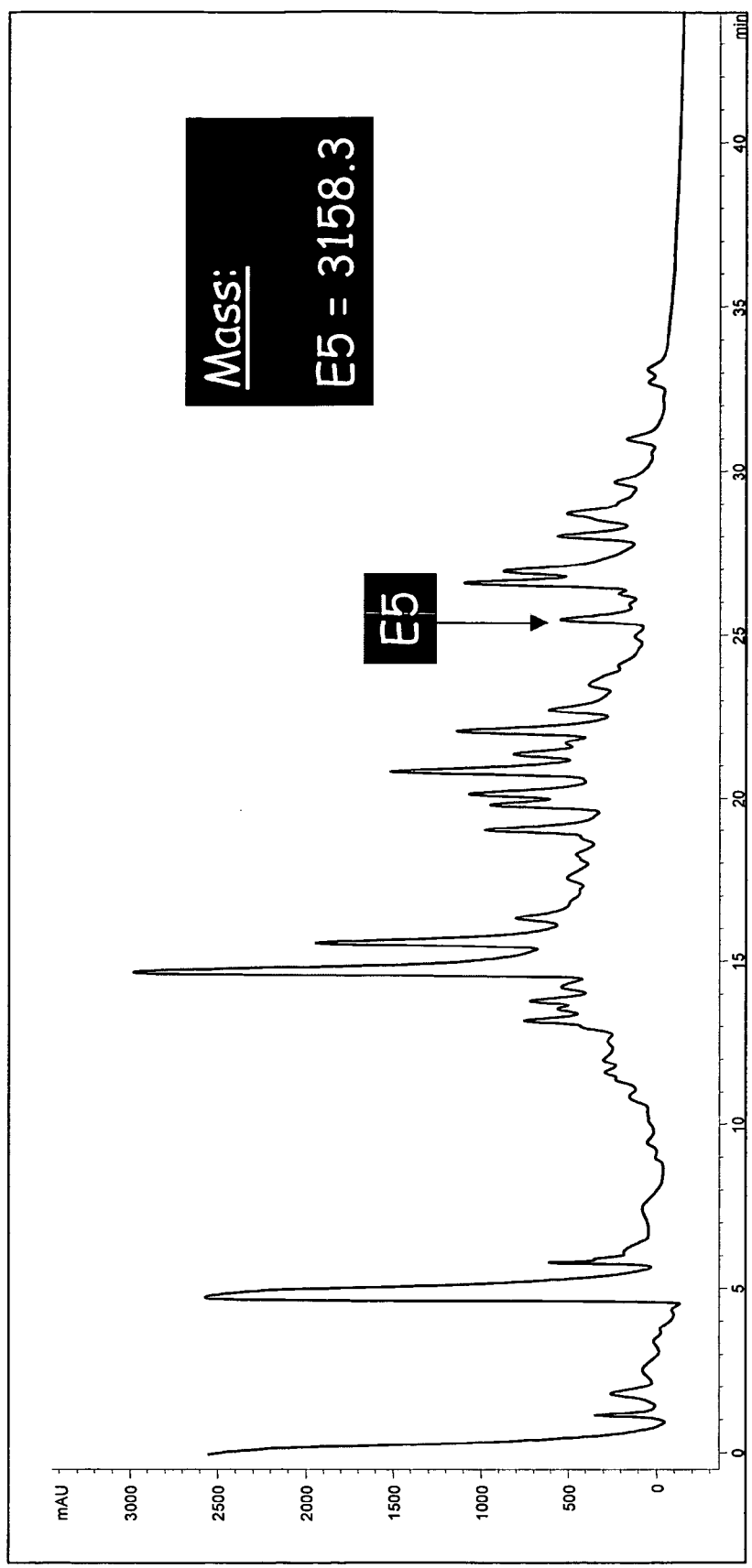
FIG. 1 depicts the HPLC profile of the crude extract from the *Viola* spp. showing the absorbance measured at 214 nm. The peak corresponding to the cyclotide (SEQ ID NO:3) is labeled "E5." The mass was observed as 3158.3 Da, which agrees well with the theoretical mass of 3159.84 Da, well within the error limit.

Embodiments of the invention are drawn to compositions and methods for impacting Homopteran insect pests, particularly plant pests. More specifically, the isolated nucleic acids of the embodiments of the invention, and fragments and variants thereof, comprise nucleotide sequences that encode pesticidal polypeptides (e.g., proteins). The disclosed pesticidal proteins are biologically active (e.g., pesticidal) against insect pests such as insect pests of the order Homoptera. Insect pests of interest include, but are not limited to: corn plant hopper (*Peregrinus maidis*) and soybean aphid (*Aphis glycines*).

Other embodiments of the invention include compositions comprising isolated nucleic acids, and fragments and variants thereof, that encode pesticidal polypeptides, expression cassettes comprising nucleotide sequences of embodiments of the invention, isolated pesticidal proteins, and pesticidal compositions. Embodiments of the invention further provide plants and microorganisms transformed with these novel nucleic acids, and methods involving the use of such nucleic acids, pesticidal compositions, transformed organisms, and products thereof in impacting insect pests.

The nucleic acids and nucleotide sequences described herein may be used to transform any organism to produce the encoded pesticidal proteins. Methods are provided that involve the use of such transformed organisms to impact or control plant pests. The nucleic acids and nucleotide sequences may also be used to transform organelles such as chloroplasts (McBride et al. (1995) *Biotechnology* 13:362–365; Kota et al. (1999) *Proc. Natl. Acad. Sci. USA* 96: 1840–1845).

Embodiments of the invention further provide fragments and variants of the naturally occurring coding sequences that also encode biologically active (e.g., pesticidal) polypeptides. These nucleotide sequences find direct use in methods for impacting pests, particularly insect pests such as pests of the order Homoptera. Accordingly, embodiments of the invention provide new approaches for impacting insect pests that do not depend on the use of traditional, synthetic chemical pesticides. Some embodiments involve the discovery of naturally-occurring, biodegradable pesticides and the genes that encode them.

Embodiments of the invention also encompass nucleic acid sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. Further embodiments provide mutations which confer improved or altered properties on polypeptides comprising them. Such mutations may be utilized with any background sequence so long as the provided toxin exhibits altered or improved pesticidal activity.

Embodiments of the present invention provide, inter alia, compositions and methods for modulating the total level of polypeptides and/or altering their ratios in a plant. As used herein, the term "modulation" is intended to mean an increase or decrease in a particular character, quality, substance, or response. The compositions comprise nucleotide and amino acid sequences from various plant species.

The following definitions and methods are provided to better define the present invention and to guide those of ordinary skill in the art in the practice of embodiments of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular, 5th edition*, Springer-Verlag; New York, 1991; and Lewin, *Genes V*, Oxford University Press: New York, 1994. The nomenclature for DNA bases as set forth at 37 CFR §1.822 is used.

As used herein, the term "comprising" means "including but not limited to".

As used herein, "antimicrobial" or "antimicrobial activity" refers to antibacterial and antifungal activity, including, but not limited to the inhibition of pathogen growth.

As used herein, the terms "plant pathogen" or "plant pest" refer to any organism that can cause harm to a plant. A plant can be harmed by an inhibition or slowing of the growth of a plant, by damage to the tissues of a plant, by a weakening of the immune system of a plant, by a reduction in the resistance of a plant to abiotic stresses, by a premature death of the plant, and the like. Plant pathogens and plant pests include, but are not limited to insect pests of the order Homoptera.

As used herein, the terms "disease resistance" or "pathogen resistance" are intended to mean that the organisms avoid the disease symptoms that are the outcome of organism-pathogen interactions. That is, pathogens are prevented from causing diseases and the associated disease symptoms, or alternatively, the disease symptoms caused by the pathogen are minimized or lessened.

As used herein, the terms "pesticidal activity" and "insecticidal activity" are used synonymously to refer to activity of an organism or a substance (such as, for example, a protein) that can be measured by but is not limited to pest mortality, pest weight loss, pest repellency, and other behavioral and physical changes of a pest after feeding and exposure for an appropriate length of time. In this manner, pesticidal activity impacts at least one measurable parameter of pest fitness. Accordingly, "pesticidal activity" and "insecticidal activity" include, but are not limited to, damage caused by plant Homopteran insect pests. For example "pesticidal proteins" are proteins that display pesticidal activity by themselves or in combination with other proteins. Endotoxins are pesticidal proteins. Other examples of pesticidal proteins include, e.g., pentin-1 (see U.S. Pat. Nos. 6,057,491 and 6,339,144). A "pesticidal agent" will act similarly to suppress, control, and/or kill an invading pathogen.

An "insecticidal composition" is intended to mean that the compositions of embodiments of the invention have activity against plant insect pathogens; including insect pests of the order Homoptera, and thus are capable of suppressing, controlling, and/or killing the invading insect. An insecticidal composition of the embodiments of the invention will reduce the symptoms resulting from insect challenge by at least about 5% to about 50%, at least about 10% to about 60%, at least about 30% to about 70%, at least about 40% to about 80%, or at least about 50% to about 90% or greater. Hence, the methods of the embodiments of the invention can be utilized to protect organisms, particularly plants, from invading insects.

Assays that measure insecticidal activity are commonly known in the art, such as insect-feeding bioassays. See, for example, Marrone et al. (1985) *J. Econ. Entomol.* 78:290–293 and Czapla and Lang (1990) *J. Econ. Entomol.* 83:2480–2485, herein incorporated by reference. The preferred developmental stage for testing for pesticidal activity is larvae or immature forms of these above mentioned insect pests. The insects may be reared in total darkness at from about 20° C. to about 30° C. and from about 30% to about 70% relative humidity. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

Compositions and methods for controlling Homopteran insect pests are provided in the embodiments of the invention. The insecticidal compositions comprise cyclotide nucleotide and amino acid sequences. Particularly, the plant nucleic acid and amino acid sequences and fragments and variants thereof set forth herein possess insecticidal activity. Accordingly, the compositions and methods are useful in protecting plants against Homopteran insect pests. Additionally provided are transformed plants, plant cells, plant tissues and seeds thereof.

The compositions of the embodiments of the invention can be used in a variety of methods whereby the protein products can be expressed in crop plants to function as insecticidal proteins. The compositions of the embodiments of the invention may be expressed in a crop plant such as maize or soybean to function as an insecticidal agent. Expression of the proteins of the invention can also be altered, resulting in changes or modulation of the level, tissue, or timing of expression in order to achieve enhanced insect resistance.

The coding sequence for the cyclotide can be used in combination with a promoter that is introduced into a crop plant. In one embodiment, a high-level expressing constitutive promoter may be utilized and would result in high levels of expression of the cyclotide. In other embodiments, the coding sequence may be operably linked to a tissue-preferred promoter to direct the expression to a plant tissue known to be susceptible to an insect. Likewise, manipulation of the timing of expression may be utilized. For example, by judicious choice of a promoter, expression can be enhanced early in plant growth to prime the plant to be responsive to insect attack. Likewise, pathogen inducible promoters can be used wherein expression of the cyclotide is turned on in the presence of the insect. If desired, a transit peptide can be utilized to direct cellular localization of the protein product. In this manner, the native transit peptide or a heterologous transit peptide can be used. However, it is recognized that both extracellular expression and intracellular expression are encompassed by the methods of the invention.

Sequences of the invention, as discussed in more detail below, encompass coding sequences, antisense sequences, and fragments and variants thereof. Expression of the sequences of the invention can be used to modulate or regulate the expression of corresponding cyclotide proteins.

The compositions and methods of the invention can be used for enhancing resistance to plant Homopteran insect pests. The method involves stably transforming a plant with a nucleotide sequence capable of modulating the plant insect defense system operably linked with a promoter capable of driving expression of a gene in a plant cell. By "enhancing resistance" increasing the tolerance of the plant to insects is intended. That is, the cyclotide may slow or prevent insect infection and/or spread.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through, for example, antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment that result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products.

Consequently, an isolated polynucleotide comprising a nucleotide sequence of at least 30 contiguous nucleotides derived from the nucleotide sequence of SEQ ID NOs: 1, 4, or 5 and its complement may be used in methods of selecting an isolated polynucleotide that affects the expression of a plant cyclotide polypeptide in a host cell. For example, an isolated polynucleotide comprising at least 30, at least 40, at least 50, at least 60 or at least any number of nucleotides up to the full length of SEQ ID NOs:1, 4 or 5. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide or an isolated chimeric gene; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Specificity in hybridization is typically the function of post-hybridization washes, the critical factors being the ionic strength and temperature of the final wash solution. The thermal melting point ($T_m$) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). Also see Sambrook et al. (1989) *Molecular Cloning: A Laboratory Manual* (2d ed., Cold Spring Harbor Laboratory Press, Plainview, N.Y.).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl, 0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. for at least 4 hours, often up to 12 hours or longer, and a final wash in 0.1×SSC at 60 to 65° C. for at least 20 minutes, for example 30 minutes, 40 minutes, 50 minutes, or 60 minutes. Optionally, wash buffers may comprise about 1% SDS. Duration of hybridization is generally less than about 24 hours, usually about 4 to about 12 hours.

Thus, isolated sequences that encode a cyclotide polypeptide and which hybridize under stringent conditions to the cyclotide sequences disclosed herein, or to fragments thereof, are encompassed by embodiments of the invention.

Substantially similar nucleic acid fragments of the invention may also be characterized by the percent identity of the amino acid sequences that they encode. For example, isolated nucleic acids which encode a polypeptide with a given percent sequence identity to the polypeptide of SEQ ID NOs: 2, 3 or 6 are disclosed. Identity can be calculated using, for example, the BLAST, CLUSTALW or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99%.

Methods of alignment of sequences for comparison are well known in the art. Thus, the determination of percent identity between any two sequences can be accomplished using a mathematical algorithm. Examples of such mathematical algorithms include, but are not limited to, the algorithm of Myers and Miller (1988) *CABIOS* 4:11–17; the alignment algorithm of Smith et al. (1981) *Adv. Appl. Math.* 2:482; the alignment algorithm of Needleman and Wunsch (1970) *J. Mol. Biol.* 48:443–453; the alignment method of Pearson and Lipman (1988) *Proc. Natl. Acad. Sci. USA* 85:2444–2448; the algorithm of Karlin and Altschul (1990) *Proc. Natl. Acad. Sci. USA* 87:2264, as modified in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997); and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915). Alignments using these programs can be performed using the default parameters. As used herein "default values" will mean any set of values or parameters which originally load with the software when first initialized.

The GAP program uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each be 0, 1, 2, 3, 4, 5, 6, 7, 8, 9, 10, 15, 20, 25, 30, 35, 40, 45, 50, 55, 60, 65 or greater, up to and including 200.

The CLUSTAL program is well described by Higgins et al. (1988) *Gene* 73:237-244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307-331. The ALIGN and the ALIGN PLUS programs are based on the algorithm of Myers and Miller (1988) supra.

The BLAST (Basic Local Alignment Search Tool) programs of Altschul et al. (1993) *J. Mol. Biol.* 215:403–410 are based on the algorithm of Karlin and Altschul (1990) supra. BLAST nucleotide searches can be performed with the BLASTN program, which searches a nucleotide query against a nucleotide database, to obtain nucleotide sequences homologous to a nucleotide sequence encoding a protein of the invention. BLAST protein searches can be performed with the BLASTX program, which searches a nucleotide query against a peptide database, to obtain amino acid sequences homologous to a protein or polypeptide of the invention. The TBLASTN program provides for a peptide query against a nucleotide database, while the TBLASTX program allows for a nucleotide query against a nucleotide database with the translation of both to protein. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules (see Altschul et al. (1997) supra). When utilizing any BLAST program the default parameters of the respective programs can be used. Alignment may also be performed manually by inspection.

An "equivalent program" refers to any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e, gaps) compared to the reference sequence for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length form of the specified protein.

The term "substantial identity" of polynucleotide sequences means that a polynucleotide comprises a sequence that has at least 70% sequence identity, including at least 75%, 80%, 85%, 86%, 87%, 88%, 89%, 90%, 91%, 92%, 93%, 94%, 95%, 96%, 97%, 98%, or 99% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, including at least 70%, 75%, 80%, 85%, 90%, 91%, 92%, 93%, 94%, 95%, 96%, 97%, 98%, and 99%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a peptide indicates that a peptide comprises a sequence with at least 70% sequence identity to a reference sequence, including 80%, 85%, 90%, 91%, 92%, 93%, 94%, 95%, 96%, 97%, 98%, or 99% sequence identity to the reference sequence over a specified comparison window. Optimal alignment may be conducted using the homology alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as the BLAST programs discussed elsewhere in this specification. (Altschul et al. (1993) supra).

Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Fragments and variants of the disclosed nucleotide sequences and proteins encoded thereby are also encompassed by the present invention. By "fragment" a portion of the nucleotide sequence or a portion of the amino acid sequence, and hence protein, encoded thereby is intended. The nucleic acid fragments of the instant invention may be used to isolate cDNAs and genes encoding homologous proteins from the same or other plant species.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies. "PCR" or "polymerase chain reaction" is a technique used for the amplification of specific DNA segments (U.S. Pat. Nos. 4,683,195 and 4,800,159).

Genes encoding other plant cyclotides, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook et al. (1989), supra). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci.* USA 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (or at least 40, or at least 30) contiguous nucleotides derived from the nucleotide sequence set forth in SEQ ID NOs: 1, 4 or 5, and its complement, may be used in such methods to obtain a nucleic acid fragment encoding a substantial portion of an amino acid sequence of a polypeptide of the present invention.

Embodiments of the invention relate to a method of obtaining a nucleic acid fragment encoding a substantial portion of a cyclotide polypeptide comprising the steps of: synthesizing an oligonucleotide primer comprising a nucleotide sequence of at least 10, at least 20, or at least 30 or more contiguous nucleotides derived from the nucleotide sequence set forth in SEQ ID NOs:1, 4, or 5, and its complement; and amplifying a nucleic acid fragment using the oligonucleotide primer. The amplified nucleic acid fragment preferably will encode a portion of a plant cyclotide polypeptide.

Availability of the instant nucleotide and deduced amino acid sequences facilitates immunological screening of cDNA expression libraries. Synthetic peptides representing portions of the cyclotide amino acid sequences may be synthesized. These peptides can be used to immunize animals to produce polyclonal or monoclonal antibodies with specificity for peptides or proteins comprising the amino acid sequences. These antibodies can then be used to screen cDNA expression libraries to isolate full-length cDNA clones of interest (Lerner (1984) *Adv. Immunol.* 36:1–34; Sambrook et al. (1989) supra).

Fragments of a nucleotide sequence may encode protein fragments that retain the biological activity of the native protein and hence have cyclotide activity, for example, insecticidal activity, and thereby affect responses to pathogens. Alternatively, fragments of a nucleotide sequence that are useful as hybridization probes generally do not encode protein fragments retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a cyclotide nucleotide sequence that encodes a biologically active portion of a cyclotide protein of the invention will encode at least 10, 15, 25, 30, 50, 100, contiguous amino acids, or up to the total number of amino acids present in a full-length protein of the embodiments. Fragments of a cyclotide nucleotide sequence that are useful as hybridization probes for PCR primers generally need not encode a biologically active portion of a cyclotide protein.

Thus, a fragment of a cyclotide nucleotide sequence may encode a biologically active portion of a cyclotide protein, or it may be a fragment that can be used as a hybridization probe or PCR primer using methods disclosed herein. A biologically active portion of a cyclotide protein can be prepared by isolating a portion of one of the cyclotide nucleotide sequences of the invention, expressing the encoded portion of the cyclotide protein (e.g., by recombinant expression in vitro), and assessing the activity of the encoded portion of the cyclotide protein. Nucleic acid molecules that are fragments of a cyclotide nucleotide sequence comprise at least 16, 20, 30, 40, 50, 75, 100, 150, 200, 250, or 300 nucleotides, or up to the number of nucleotides present in a full-length cyclotide nucleotide sequence disclosed herein.

By "variants" substantially similar sequences are intended. For nucleotide sequences, conservative variants include those sequences that, because of the degeneracy of the genetic code, encode the amino acid sequence of one of the cyclotide polypeptides of the invention. Naturally occurring allelic variants such as these can be identified with the use of well-known molecular biology techniques, such as, for example, with polymerase chain reaction (PCR) and hybridization techniques as outlined herein. Variant nucleotide sequences also include synthetically derived nucleotide sequences, such as those generated, for example, by using site-directed mutagenesis but which still encode a cyclotide protein. Generally, variants of a particular nucleotide sequence of the invention will have at least about 50%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs described elsewhere herein using default parameters.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the embodiments are biologically active, that is they continue to possess the desired biological activity of the native protein, that is, cyclotide activity as described herein, for example, insecticidal activity. Such variants may result from, for example, genetic polymorphism or from human manipulation. Biologically active variants of a native cyclotide protein of the invention will have at least about 40%, 50%, 60%, 65%, 70%, 75%, 80%, 85%, 90%, 91%, 92%, 93%, 94%, 95%, 96%, 97%, and including at least about 98%, 99% or more sequence identity to the amino acid sequence for the native protein as determined by sequence alignment programs described elsewhere herein using default parameters. A biologically active variant of the native protein may differ from that protein by as few as 1–15 amino acid residues, as few as 1–10, such as 6–10, as few as 5, as few as 4, 3, 2, or even 1 amino acid residue.

The polypeptides of the embodiments may be altered in various ways including amino acid substitutions, deletions, truncations, and insertions. Novel proteins having properties of interest may be created by combining elements and fragments of proteins of the present invention with other proteins as well. Methods for such manipulations are generally known in the art. For example, amino acid sequence variants of the cyclotide proteins can be prepared by mutations in the DNA. Methods for mutagenesis and nucleotide sequence alterations are well known in the art. See, for example, Kunkel (1985) *Proc. Natl. Acad. Sci.* USA 82:488–492; Kunkel et al. (1987) *Methods in Enzymol.* 154:367–382; U.S. Pat. No. 4,873,192; Walker and Gaastra, eds. (1983) *Techniques in Molecular Biology* (Macmillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both naturally occurring sequences as well as mutant forms. Likewise, the proteins of the invention encompass naturally occurring proteins as well as variations and modified forms thereof. Such variants will continue to possess the desired cyclotide activity (for example, insecticidal activity) or defense response activity. Obviously, mutations that will be made in the DNA encoding the variant must not place the sequence out of reading frame and preferably will not create complementary regions that could produce secondary mRNA structure (see EP Patent Publication No. 0 075 444 B1).

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. Biological activity of the variant polypeptides of the present invention can be assayed by any method known in the art, such as those already discussed and referenced elsewhere in this application.

Variant nucleotide sequences and proteins also encompass sequences and proteins derived from a mutagenic and recombinogenic procedure such as DNA shuffling. With such a procedure, one or more different cyclotide coding sequences can be manipulated to create a new cyclotide protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell. Determination of preferred codons can be based on a survey of genes derived from the host cell where sequence information is available. For example, the codon frequency tables available on the world wide web at Kazusa.or.jp/codon/ may be used to determine preferred codons for a variety of organisms. See also Campbell and Gowri (1990) *Plant Physiol.* 92:1–11; Murray et al. (1989) *Nucleic Acids Res.* 17:477–498, U.S. Pat. Nos. 5,380,831 and 5,436,391; and the information found on the world wide web at agron.missouri.edu/mnl/77/10simmons.html; herein incorporated by reference.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood to be within the scope of the invention and to comprise, for example, plant cells, protoplasts, tissues, callus, embryos, as well as flowers, ovules, stems, fruits, leaves, roots originating in transgenic plants or their progeny previously transformed with a DNA molecule of the invention and therefore consisting at least in part of transgenic cells.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

"Coding sequence" refers to a nucleotide sequence that codes for a specific amino acid sequence. As used herein, the terms "encoding" or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence may consist of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". While new promoters of various types useful in plant cells are constantly being discovered; numerous examples of known promoters may be found, for example, in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

Other methods known to enhance translation and/or mRNA stability can also be utilized, for example, introns, such as the maize ubiquitin intron (Christensen and Quail (1996) *Transgenic Res.* 5:213–218 and Christensen et al. (1992) *Plant Molecular Biology* 18:675–689) or the maize AdhI intron (Kyozuka et al. (1991) *Mol. Gen. Genet* 228: 4048 and Kyozuka et al. (1990) *Maydica* 35:353–357), and the like. Various intron sequences have been shown to enhance expression, particularly in monocotyledonous cells. The introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., (1987) *Genes Develop.* 1:1183–1200). In the same experimental system, the intron from the maize bronze1 gene had a similar effect in enhancing expression. The AdhI intron has also been shown to enhance CAT expression 12-fold (Mascarenhas et al. (1990) *Plant Mol. Biol.* 6:913–920). Intron sequences have routinely been incorporated into plant transformation vectors, typically within the non-translated leader.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

As used herein, "5' leader sequence", "translation leader sequence" or "5' non-coding sequence" refer to that DNA sequence portion of a gene between the promoter and coding sequence that is transcribed into RNA and is present in the fully processed mRNA upstream (5') of the translation start codon. A 5' non-translated leader sequence is usually characterized as that portion of the mRNA molecule which most typically extends from the 5'CAP site to the AUG protein translation initiation codon.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide.

"Altered levels" or "altered expression" refers to the production of gene product(s) in transgenic organisms in amounts or proportions that differ from that of normal or non-transformed organisms.

"Null mutant" refers here to a host cell that either lacks the expression of a certain polypeptide or expresses a polypeptide which is inactive or does not have any detectable expected enzymatic function.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). The following terms are of relevance. "Mature protein", "preproprotein" or "prepropeptide" refer to a post-translationally processed polypeptide; i.e., one from which any pre- or propeptides present in the primary translation product have been removed. "Precursor protein" refers to the primary product of translation of mRNA; i.e., with pre- and propeptides still present. Pre- and propeptides may be, but are not limited to, intracellular localization signals. The form of the translation product with only the signal peptide removed but not further processing yet is called a "propeptide" or "proprotein". The fragments to be removed may themselves are also referred to as "propeptides". The skilled artisan will need to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptides may play a role in aiding correct peptide folding.

A "chloroplast transit peptide" is an amino acid sequence that is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence that is translated in conjunction with a protein and directs the protein to the secretory system (see Chrispeels (1991) *Ann. Rev. Plant Phys. Plant Mol. Biol.* 42:21–53). If the protein is to be directed to a vacuole, a vacuolar targeting signal can further be added, or if to the endoplasmic reticulum, an endoplasmic reticulum retention signal may be added. If the protein is to be directed to the nucleus, any signal peptide present should be removed and instead a nuclear localization signal included (see Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. (1989) supra.

In another embodiment, this invention concerns viruses and host cells comprising either the chimeric genes of the invention as described herein or an isolated polynucleotide of the invention as described herein. Examples of host cells that can be used to practice the invention include, but are not limited to, yeast, bacterial, fungal, insect, amphibian, mammalian, and plant cells.

As used herein, "host cell" refers to a cell which comprises a heterologous nucleic acid sequence of the invention. Host cells may be prokaryotic cells such as *E. coli*, or eukaryotic cells such as yeast, fungal, insect, amphibian, mammalian or plant cells. Host plant cells include monocotyledonous or dicotyledonous plant cells. One example of a monocotyledonous host cell is a maize host cell. One example of a dicotyledonous host cell is a soybean host cell.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' non-coding sequences encoding transcription termination signals may also be provided. The instant chimeric gene may also comprise one or more introns in order to facilitate gene expression.

The cyclotide sequences of the invention are provided in expression cassettes or DNA constructs for expression in the plant of interest. The cassette will include 5' and 3' regulatory sequences operably linked to a cyclotide sequence of the invention. The cassette may additionally contain at least one additional gene to be cotransformed into the organism. Alternatively, the additional gene(s) can be provided on multiple expression cassettes.

Such an expression cassette is provided with a plurality of restriction sites for insertion of the cyclotide sequence to be under the transcriptional regulation of the regulatory regions. The expression cassette may additionally contain selectable marker genes.

The expression cassette will include in the 5'–3' direction of transcription, a transcriptional initiation region (i.e., a promoter), translational initiation region, a cyclotide polynucleotide sequence of the invention, a translational termination region and, optionally, a transcriptional termination region functional in the host organism. The transcriptional initiation region, the promoter, may be native or analogous or foreign or heterologous to the plant host. Additionally, the promoter may be the natural sequence or alternatively a synthetic sequence. "Foreign" is intended to mean that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of cyclotides in the host cell (e.g., plant or plant cell). Thus, the phenotype of the host cell (e.g., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase (NOS) termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Gallie et al. (1995) *Gene* 165(2): 233–238); MDMV leader (Maize Dwarf Mosaic Virus), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci.* USA 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993)

Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724, and US Patent Publications US 20030083480 A1 (now abandoned) and US 20040082770. Such disclosures are herein incorporated by reference.

The above list of selectable marker genes is not meant to be limiting. Any selectable marker gene can be used in the present invention.

In specific embodiments, methods for increasing pathogen resistance in a plant comprise stably transforming a plant with a DNA construct comprising an antipathogenic nucleotide sequence of the invention operably linked to a promoter that drives expression in a plant. Such methods find use in agriculture particularly in limiting the impact of plant pathogens on crop plants. While the choice of promoter will depend on the desired timing and location of expression of the anti-pathogenic nucleotide sequences, examples of promoters include constitutive and pathogen-inducible promoters.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, herein incorporated by reference.

Generally, it will be beneficial to express the gene from an inducible promoter, for example from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also WO 99/43819 published Sep. 9, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters. See, for example, Gatz et al. (1991) *Mol. Gen. Genet* 227:229–237, and U.S. Pat. Nos. 5,814,618 and 5,789,156; herein incorporated by reference.

Tissue-preferred promoters can be utilized to target enhanced cyclotide expression within a particular plant tissue. Tissue-preferred promoters include Yamamoto et al. (1997) *Plant J.* 12(2):255–265; Kawamata et al. (1997) *Plant Cell Physiol.* 38(7):792–803; Hansen et al (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β3-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

The method of transformation/transfection is not critical to the instant invention. Various methods of transformation or transfection are currently available. As newer methods are available to transform crops or other host cells they may be used with the instant invention. Accordingly, a wide variety of methods have been developed to insert a DNA sequence into the genome of a host cell to obtain the transcription and/or translation of the sequence to effect phenotypic changes in the organism. The nucleic acid fragments of the instant invention may be used to create transgenic plants in which the disclosed plant cyclotides are present at higher or lower levels than normal or in cell types or developmental stages in which they are not normally found. This would have the effect of altering the level of disease (e.g., fungal) and pathogen resistance in those cells. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. Nos. 5,563,055 and 5,981,840), direct gene transfer (Paszkowski et al. (1984) *EMBO J.* 3:2717–2722), and ballistic particle acceleration (see, for example, U.S. Pat. Nos. 4,945,050; 5,879,918; 5,886,244; and 5,932,782; McCabe et al. (1988) *Biotechnology* 6:923–926); and Lec1 transformation. Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783 and 5,324,646; Tomes et al. (1995) in Plant Cell, Tissue, and Organ Culture: Fundamental Methods, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (*Liliaceae*); De Wet et al. (1985) in The Experimental Manipulation of Ovule Tissues, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) Nature *Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp., *Pisum* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Hydrangea macrophylla*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In certain embodiments of the present invention, crop plants are used (for example, corn, soybean, alfalfa, sunflower, *Brassica*, cotton, safflower, peanut, sorghum, wheat, millet, tobacco, etc.).

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229–235 and Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Such antimicrobial proteins can be used for any application including coating surfaces to target microbes as described further infra.

Synthesis of heterologous nucleotide sequences in yeast is well known. Sherman, et al. (1982) *Methods in Yeast Genetics* (Cold Spring Harbor Laboratory) is a well recognized work describing the various methods available to produce proteins in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like, as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773–781). Additionally, gene sequences to control replication in the host cell may be incorporated into the vector such as those found in bovine papilloma virus type-vectors. Saveria-Campo (1985) "Bovine Papilloma Virus DNA a Eukaryotic Cloning Vector," in *DNA Cloning Vol. II: A Practical Approach*, ed. D. M. Glover (IRL Press, Arlington, Va.), pp. 213–238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler (1997) *Biochemical Methods in Cell Culture and Virology* (Dowden, Hutchinson and Ross, Inc.).

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, northern analysis of mRNA expression, western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum (ER) localization (Chrispeels (1991) supra), or nuclear localization signals (Raikhel (1992) supra) with or without removing targeting sequences that are already present.

Unlike the promoter, which acts at the transcriptional level, such targeting information is part of the initial translation product. The location of the protein in different compartments of the cell may make it more efficacious or make it interfere less with the functions of the cell. For example, one may produce a protein preceded by a signal peptide, which directs the translation product into the ER, by including in the chimeric construct sequences encoding a signal peptide (such sequences may also be called the "signal sequence"). The signal sequence used could be that associated with the gene encoding the polypeptide, or it may be taken from another gene. There are many signal peptides described in the literature, and they are largely interchangeable (Raikhel N, Chrispeels M J (2000) Protein sorting and vesicle traffic. In B Buchanan, W Gruissem, R Jones, eds, Biochemistry and Molecular Biology of Plants. American Society of Plant Physiologists, Rockville, Md., pp 160–201, herein incorporated by reference). The addition of a signal peptide will result in the translation product entering the ER (in the process of which the signal peptide itself is removed from the polypeptide), but the final intracellular location of the protein depends on other factors, which may be manipulated to result in localization most appropriate for the pathogen and cell type.

The default pathway, that is, the pathway taken by the polypeptide if no other targeting labels are included, results in secretion of the polypeptide across the cell membrane (Raikhel and Chrispeels, (2000) supra). This will leave the peptide between the cell membrane and cell wall, which will often be a suitable location. Other pathogens may be more effectively combated by locating the peptide within the cell. This can be accomplished, for example, by adding an ER retention signal encoding sequence to the sequence to the gene. Methods and sequences for doing this are described in Raikhel and Chrispeels (2000) supra; for example, adding sequences encoding the amino acids K, D, E and L in that order, or variations thereof described in the literature, to the end of the protein coding portion of the polypeptide will accomplish this. Alternatively, the use of vacuolar targeting labels such as those described by Raikhel and Chrispeels (2000) supra, in addition to a signal peptide will result in localization of the peptide in a vacuolar structure. Use of a plastid transit peptide encoding sequence instead of a signal peptide encoding sequence will result in localization of the polypeptide in the plastid of the cell type chosen. One of skill in the art could also envision localizing the polypeptide in other cellular compartments by addition of suitable targeting information. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one that allows large numbers of samples to be processed rapidly, since it will be expected that a large number of transformants will be negative for the desired phenotype.

The instant polypeptides are useful in methods for impacting a plant pathogen comprising introducing into a plant or cell thereof at least one nucleotide construct comprising a nucleotide sequence of the invention operably linked to a promoter that drives expression of an operably linked sequence in plant cells, wherein said nucleotide sequence is selected from the group consisting of: a nucleotide sequence set forth in SEQ ID NOs: 1, 4 or 5; a nucleotide sequence that encodes a polypeptide having the amino acid sequence set forth in SEQ ID NOs: 2, 3 or 6; a nucleotide sequence characterized by at least 85% sequence identity to the nucleotide sequences set forth in SEQ ID NOs: 1, 4 or 5; a nucleotide sequence characterized by at least 90% sequence identity to the nucleotide sequence set forth in SEQ ID NOs: 1, 4 or 5; a nucleotide sequence characterized by at least 95% sequence identity to the nucleotide sequence set forth in SEQ ID NOs: 1, 4 or 5; and a nucleotide sequence that comprises the complement of any one of the above.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Polyclonal cyclotide antibodies can be prepared by immunizing a suitable subject (e.g., rabbit, goat, mouse, or other mammal) with a cyclotide agent immunogen. The anti-cyclotide antibody titer in the immunized subject can be monitored over time by standard techniques, such as with an enzyme linked immunosorbent assay (ELISA) using immobilized antimicrobial polypeptides. At an appropriate time after immunization, e.g., when the anti-cyclotide agent antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., New York); and Lerner (1981) *Yale J. Biol. Med.* 54:387–402).

Alternative to preparing monoclonal antibody-secreting hybridomas, a monoclonal anti-cyclotide antibody can be identified and isolated by screening a recombinant combinatorial immunoglobulin library (e.g., an antibody phage display library) with a cyclotide to thereby isolate immunoglobulin library members that bind the defensive agent. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246: 1275–1281; Griffiths et al. (1993) *EMBO J.* 12:725–734. The antibodies can be used to identify homologs of the cyclotides of the invention.

All or a substantial portion of the polynucleotides of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Sambrook et al. (1989) supra) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. in: *Nonmammalian Genomic Analysis: A Practical Guide*, Academic Press, New York), 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes eta. (1995) *Proc. Natl. Acad. Sci. USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

The methods of the invention can be used with other methods available in the art for enhancing insect resistance in plants. For example, embodiments of the invention encompass any one of a variety of second nucleotide sequences being utilized such that, when expressed in a plant, they help to increase the resistance of a plant to insect pests. It is recognized that such second nucleotide sequences may be used in either the sense or antisense orientation depending on the desired outcome.

Furthermore, embodiments of the present invention may be effective against Homoptera such as aphids, planthoppers, leafhoppers, scale insects and others. The Homopteran order includes such families as the Adelgidae (adelgids), Aleyrodidae (whiteflies), Aphididae (aphids), Asterolecanidae (pit scales), Cercopidae (froghoppers or spittlebugs), Cicadellidae (leafhoppers), Cicadidae (cicadas), Cixiidae, Coccidae (soft scales), Dactylopiidae (dactylopiid or cochineal scales), Delphacidae (planthoppers), Diaspididae (armored scales), Eriococcidae (eriococcid scales), Flatidae (flatid planthoppers), Issidae (issid planthoppers), Margarodidae (margarodid scales), Membracidae (treehoppers), Ortheziidae (ensign scales), Phoenicococcidae (phoenicococcid scales), Phylloxeridae (phylloxerans), Pseudococcidae (mealybugs) and Psyllidae (psyllids).

The methods of the invention can be used with other methods available in the art for enhancing disease and pathogen resistance in plants. Similarly, the antimicrobial compositions described herein may be used alone or in combination with other nucleotide sequences, polypeptides, or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens.

Proteins, peptides, and lysozymes that naturally occur in insects (Jaynes et al. (1987) *Bioassays* 6:263–270), plants (Broekaert et al. (1997) *Critical Reviews in Plant Sciences* 16:297–323), animals (Vunnam et al. (1997) *J. Peptide Res.* 49:59–66), and humans (Mitra and Zang (1994) *Plant Physiol.* 106:977–981; Nakajima et al. (1997) *Plant Cell Reports* 16:674–679) are also a potential source of plant pathogen resistance (Ko, K. (2000) on the world wide web at Scisoc.org/feature/BioTechnology/antimicrobial.html). Examples of such plant resistance-conferring sequences include those encoding sunflower rhoGTPase-Activating Protein (rhoGAP), lipoxygenase (LOX), Alcohol Dehydrogenase (ADH), and *Sclerotinia*-Inducible Protein-1 (SCIP-1) described in U.S. patent application Ser. No. 09/714,767 now U.S. Pat. No. 6,709,865 herein incorporated by reference. These nucleotide sequences enhance plant disease resistance through the modulation of development, developmental pathways, and the plant pathogen defense system. It is recognized that such second nucleotide sequences may be used in either the sense or antisense orientation depending on the desired outcome.

In another embodiment, the cyclotides comprise isolated polypeptides of the invention. The cyclotides of the invention find use in the decontamination of plant pathogens during the processing of grain for animal or human food consumption; during the processing of feedstuffs, and during the processing of plant material for silage. In this embodiment, the cyclotides of the invention are presented to grain, plant material for silage, or a contaminated food crop, or during an appropriate stage of the processing procedure, in amounts effective for antimicrobial activity. The compositions can be applied to the environment of a plant pathogen by, for example, spraying, atomizing, dusting, scattering, coating or pouring, introducing into or on the soil, introducing into irrigation water, by seed treatment, or dusting at a time when the plant pathogen has begun to appear or before the appearance of pests as a protective measure. It is recognized that any means that bring the cyclotide polypeptides in contact with the plant pathogen can be used in the practice of the invention.

Additionally, the compositions can be used in formulations used for their antimicrobial activities. Methods are provided for controlling plant pathogens comprising applying a decontaminating amount of a polypeptide or composition of the invention to the environment of the plant pathogen. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn4, 7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of a primary composition, which requires dilution with a suitable quantity of water or other diluent before application. The decontaminating concentration will vary depending upon the nature of the particular formulation, specifically, whether it is a concentrate or to be used directly.

In a further embodiment, the compositions, as well as the polypeptides of the present invention can be treated prior to formulation to prolong the activity when applied to the environment of a plant pathogen as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.)).

In an embodiment of the invention, the compositions of the invention comprise a microbe having stably integrated the nucleotide sequence of a cyclotide agent. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the cyclotides to potential target crops. Epiphytes can be, for example, gram-positive or gram-negative bacteria.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a cyclotide agent of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the proteins of the invention from environmental degradation and inactivation.

Such microorganisms include bacteria, algae, and fungi. Illustrative prokaryotes, both Gram-negative and -positive, include Enterobacteriaceae, such as *Escherichia*, *Erwinia*, *Shigella*, *Salmonella*, and *Proteus*; Bacillaceae; Rhizobiaceae, such as *Rhizobium*; Spirillaceae, such as photobacterium, *Zymomonas*, *Serratia*, *Aeromonas*, *Vibrio*, *Desulfovibrio*, *Spirillum*; Lactobacillaceae; Pseudomonadaceae, such as *Pseudomonas* and *Acetobacter*; Azotobacteraceae; and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula*, *Aureobasidium*, *Sporobolomyces*, and the like.

Of particular interest are microorganisms, such as bacteria, e.g., *Pseudomonas*, *Erwinia*, *Serratia*, *Klebsiella*, *Xanthomonas*, *Streptomyces*, *Rhizobium*, *Rhodopseudomonas*, *Methylius*, *Agrobacterium*, *Acetobacter*, *Lactobacillus*, *Arthrobacter*, *Azotobacter*, *Leuconostoc*, and *Alcaligenes*; fungi, particularly yeast, e.g., *Saccharomyces*, *Pichia*, *Cryptococcus*, *Kluyveromyces*, *Sporobolomyces*, *Rhodotorula*, *Aureobasidium*, and *Gliocladium*. Of particular interest are such phytosphere bacterial species as *Pseudomonas syringae*, *Pseudomonas fluorescens*, *Serratia marcescens*, *Acetobacter xylinum*, *Agrobacteria*, *Rhodopseudomonas spheroides*, *Xanthomonas campestris*, *Rhizobium melioti*, *Alcaligenes entrophus*, *Clavibacter xyli*, and *Azotobacter vinlandii*; and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces roseus*, *S. odorus*, *Kluyveromyces veronae*, and *Aureobasidium pullulans*.

The cyclotides of the invention can be used for any application including coating surfaces to target microbes. In this manner, target microbes include human pathogens or microorganisms. Surfaces that might be coated with the cyclotides of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The present invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention, in addition to those shown and described herein will be apparent to those skilled in the art from the foregoing description. Such modifications are also intended to fall within the scope of the appended claims.

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference.

EXAMPLES

Example 1

Extraction and Isolation of Plant Cyclotides

Tissue from *Viola* spp. (10.0 g, wet weight) was harvested from plants grown in a growth chamber under standard conditions. The *Viola* spp. tissue was ground and extracted with buffer (50 mM $Na_2HPO_4$, 50 mM $NaH_2PO_4$, 50 mM Tris-HCl, 100 mM KCl, 2 mM EDTA). The crude extract was filtered through a cotton-plug filter to remove plant debris while fine particulate matter was removed by centrifugation (Sorvall® Instruments RC5C, 15,000 rpm, 15 minutes, 4° C.). The supernatant was partitioned with n-Butanol (BuOH). The BuOH layer was dried in a speedvac and redissolved in 2 mL distilled water. The sample (100 µL/run) was fractionated by reverse phase high performance liquid chromatography, RP-HPLC.

Example 2

Fractionation by RP-HPLC

RP-HPLC was performed on a Hewlett-Packard HP1100 series using a Vydac® 300 angstrom pore size, 10 microns particle C18 column (catalog number 218TP104, Grace Vydac, W. R. Grace & Co., Columbia, Md.) and a 0–80% gradient from Solvent A (95% $H_2O$, 5% acetonitrile, 0.1% trifluoroacetic acid) to Solvent B (5% $H_2O$, 95% acetonitrile, 0.1% trifluoroacetic acid) over 40 minutes with a flow rate of 0.6 mL/min. Samples for bioassay against the target homopteran pests were collected in 96-well plates on a Foxy™ 200 fraction collector (Isco, Inc., Lincoln, Nebr.). The plates were lyophilized and assayed against different targets in replicates of three. Peptides having specific activity against *Peregrinus maidis* and *Aphis glycines* were purified to homogeneity on a capillary reverse phase C18 column (Magic 2002 HPLC System, Michrom BioResources, FUTECS, Daejon Korea) utilizing the following gradient: 10–30% Solvent B over 10 minutes followed by 30–60% Solvent B over 60 minutes; and subsequently assayed in a dose-dependent or dose-response manner.

The HPLC profile of the crude extract of *Viola* spp. is shown in FIG. 1. The eluted peak corresponding to the cyclotide of the instant invention is labeled E5, with an observed mass of 3158.3 Da.

Example 3

Mass Spectrometry

Mass spectra were acquired on a Micromass Platform LCZ instrument (Waters Mass Spectrometry Systems, Micromass Division, Manchester, U.K.) during LCMS runs. Dried samples of the crude extract were dissolved in distilled water to give a concentration of approximately 1 mg/mL, and 10 µL was injected into the solvent stream for introduction into the ionization source of the mass spectrometer. Mass spectra were obtained over the range 900–2200 $m/z^+$ and processed using the software MassLynx™, version 3.1. The gradient was started at 0% buffer B (5% $H_2O$, 95% acetonitrile, 0.1% trifluoroacetic acid) to 75% in 30 minutes with a flow rate of 50 µL. The mass of the cyclotide E5 which was obtained from the mass spectrometry procedure was 3158.3 Da.

Example 4

Production of *Viola* spp. cDNA Libraries

Total RNA from *Viola* spp. leaves was prepared by pulverizing the tissue with a mortar and pestle in liquid nitrogen and lysing cells in the presence of TRIzol™ (Invitrogen Life Technologies, Carlsbad, Calif.) according to the manufacturer's protocol. Viola leaves were harvested directly into liquid nitrogen before processing. PolyA(+) RNA was oligo(dT)-cellulose affinity column purified from total RNA using the mRNA Purification Kit (Amersham Pharmacia Biotech, CA) and following the kit's protocol in preparation for cDNA library construction. First strand cDNA synthesis was performed using Superscript II™ (Invitrogen Life Technologies) and subsequent second strand synthesis, linker addition, and directional cloning into the EcoRI and XhoI sites of pBlueScript™ SK+ (Stratagene, La Jolla, Calif.) was performed according to the instructions provided with the Stratagene cDNA kit (Stratagene). cDNA was purified using a cDNA column (Invitrogen Life Technologies) immediately prior to ligation into the vector.

Sequencing of cDNA library clones was performed using the ABI PRISM™ Big Dye Terminator Cycle Sequencing Ready reaction kit with FS AmpliTaq™ DNA polymerase (Applied Biosystems, Foster City, Calif.) and analyzed on an ABI Model 373 Automated DNA Sequencer (Applied Biosystems).

Example 5

N-Terminal Sequencing

Approximately 1.0 µg of cyclotide E5 was reduced with TCEP and alkylated with maleimide. It was subsequently cleaved with Endo-Glu C to yield a linear chain peptide. The mass of the peptide was monitored at each stage. The N-terminal tag of the cleaved species was sequenced using an automatic Edman sequencer (494 Protein Sequencer, Applied Biosystems, Foster City, Calif.) for 31 cycles. Peptide sequences corresponding to those obtained by amino acid sequencing of the Endo GluC treated actives were used to compare to the corresponding cDNA clone sequence library translated in all 6 reading frames using TBLASTN or TFASTA programs. Sequences having 100% identity to the experimentally generated amino acid sequence(s) were fully translated and their predicted molecular weight (MW) compared to the MW of purified active protein. In this way a single nucleotide sequence that encodes the exact amino acid sequence of cyclotide E5 with a theoretical mass (3159.84 Da) that closely matched the experimentally observed mass (3158.3 Da) within the error limit was identified as the nucleotide corresponding to the peptide of this invention.

The following complete amino acid sequence was obtained:

N-terminal sequence (SEQ ID NO: 3): KIPCGESCVYIGCTLTALAGCKCKNKVCYN.

Example 6

Insecticidal Activity of Cyclotide E5 Tested against Homopteran Insects *Peregrinus maidis* and *Aphis glycines*

To test for the insecticidal activity of cyclotide E5 against the target homopteran pests, the lyophilized fractionated samples were placed in 96-well microtiter plates, resuspended in $H_2O$ and added to a 20% sucrose solution as detailed below. Parafilm was stretched to just short of its breaking point and used to seal the sucrose/sample reservoir. Adult insects were then added on top of the membrane in a second chamber such that the base of the insect enclosure was the parafilm membrane. The top of the insect chamber was then sealed with plastic wrap and punctured for air exchange. The number of insects feeding from each well was determined. The assay was scored after 72 hours and nsecticidal activity was measured based on insect mortality.

Specifically, for the dose-response assay results shown in Tables 1 and 2, lyophilized RP-HPLC-pure sample was resuspended in 300 μL $H_2O$ and added to 20% sucrose in the following volumes: 60, 45, 25, 10, and 5 μL. Two replicates per dose were prepared, including two negative controls.

After 72 hours, the wells were scored for insect mortality. The following results were observed.

TABLE 1

Dose response assay for E5 against *Peregrinus maidis*

| | | | | | | | |
|---|---|---|---|---|---|---|---|
| E5 volume (μL) | 60 | 45 | 25 | 10 | 5 | 0 | 0 |
| E5 Concentration (μM) | 33.22 | 16.61 | 9.97 | 4.09 | 2.73 | 0 | 0 |
| average percent (%) insect mortality | 100 | 100 | 95 | 90 | 90 | 0 | 0 |

TABLE 2

Dose response assay for E5 against *Aphis glycines*

| | | | | | | | |
|---|---|---|---|---|---|---|---|
| E5 Volume (μL) | 60 | 45 | 25 | 10 | 5 | 0 | 0 |
| E5 Concentration (μM) | 76.35 | 57.26 | 31.81 | 12.73 | 6.36 | 0 | 0 |
| average percent (%) insect mortality | 100 | 95 | 75 | 80 | 56.5 | 10.5 | 4.2 |

---

What is claimed is:

1. An isolated nucleic acid molecule comprising a nucleotide sequence selected from the group consisting of:
   (a) the nucleotide sequence set forth in SEQ ID NO: 1, 4 or 5;
   (b) a nucleotide sequence that encodes a polypeptide having the amino acid sequence set forth in SEQ ID NO: 2, 3 or 6;
   (c) a nucleotide sequence that comprises the full length complement of (a) or (b).

2. The nucleic acid molecule according to claim 1, wherein the nucleotide sequence is optimized for expression in a plant.

3. A DNA construct comprising the nucleotide sequence of claim 1, wherein said nucleotide sequence is operably linked to a promoter that drives expression in a host cell.

4. An expression cassette comprising the DNA construct of claim 3.

* * * * *

SEQUENCE LISTING

```
<160> NUMBER OF SEQ ID NOS: 6

<210> SEQ ID NO 1
<211> LENGTH: 363
<212> TYPE: DNA
<213> ORGANISM: Viola spp.
<220> FEATURE:
<221> NAME/KEY: CDS
<222> LOCATION: (1)...(363)

<400> SEQUENCE: 1 atg gag agc tac aag aag atg cag ctt gtt ggg ttt gtg ctc ctg gcc      48
Met Glu Ser Tyr Lys Lys Met Gln Leu Val Gly Phe Val Leu Leu Ala
 1               5                  10                  15 gcc ttt gcg cta cca gca ctt gca tcg tct ttc gag aaa gat gtt atc      96
Ala Phe Ala Leu Pro Ala Leu Ala Ser Ser Phe Glu Lys Asp Val Ile
             20                  25                  30 tct gcc cat gcc atc cag gct gtt ctg gag aag agg gga tta agc aag     144
Ser Ala His Ala Ile Gln Ala Val Leu Glu Lys Arg Gly Leu Ser Lys
         35                  40                  45 ctg gag gat gat cct gtc ttg agc gct ctt gcg agc acc aaa acc atc     192
Leu Glu Asp Asp Pro Val Leu Ser Ala Leu Ala Ser Thr Lys Thr Ile
 50                  55                  60 atc tct aac cct gtc atc gaa gag gct ttg ctt agt ggt gcc agc ctg     240
Ile Ser Asn Pro Val Ile Glu Glu Ala Leu Leu Ser Gly Ala Ser Leu
 65                  70                  75                  80 gaa gct ggt aat aaa atc ccc tgc ggc gag agc tgc gtg tac att gga     288
Glu Ala Gly Asn Lys Ile Pro Cys Gly Glu Ser Cys Val Tyr Ile Gly
                 85                  90                  95 tgc aca ctc aca gcc tta gct ggg tgc aaa tgc aag aac aaa gtt tgc     336
Cys Thr Leu Thr Ala Leu Ala Gly Cys Lys Cys Lys Asn Lys Val Cys
            100                 105                 110 tac aac tct ctc caa acc aag tac tga                                  363
Tyr Asn Ser Leu Gln Thr Lys Tyr *
            115                 120
```

```
<210> SEQ ID NO 2
<211> LENGTH: 120
<212> TYPE: PRT
<213> ORGANISM: Viola spp.
<220> FEATURE:
<221> NAME/KEY: DOMAIN
<222> LOCATION: (1)...(84)
<223> OTHER INFORMATION: N-terminal pro-peptide sequence
<220> FEATURE:
<221> NAME/KEY: DOMAIN
<222> LOCATION: (57)...(84)
<223> OTHER INFORMATION: N-terminal repeat fragment
<220> FEATURE:
<221> NAME/KEY: DOMAIN
<222> LOCATION: (85)...(114)
<223> OTHER INFORMATION: Mature cyclotide sequence
<220> FEATURE:
<221> NAME/KEY: DOMAIN
<222> LOCATION: (115)...(120)
<223> OTHER INFORMATION: C-terminal fragment, excised during processing

<400> SEQUENCE: 2

Met Glu Ser Tyr Lys Lys Met Gln Leu Val Gly Phe Val Leu Leu Ala
 1               5                  10                  15

Ala Phe Ala Leu Pro Ala Leu Ala Ser Ser Phe Glu Lys Asp Val Ile
            20                  25                  30

Ser Ala His Ala Ile Gln Ala Val Leu Glu Lys Arg Gly Leu Ser Lys
        35                  40                  45

Leu Glu Asp Asp Pro Val Leu Ser Ala Leu Ala Ser Thr Lys Thr Ile
    50                  55                  60

Ile Ser Asn Pro Val Ile Glu Glu Ala Leu Leu Ser Gly Ala Ser Leu
65                  70                  75                  80

Glu Ala Gly Asn Lys Ile Pro Cys Gly Glu Ser Cys Val Tyr Ile Gly
                85                  90                  95

Cys Thr Leu Thr Ala Leu Ala Gly Cys Lys Cys Lys Asn Lys Val Cys
            100                 105                 110

Tyr Asn Ser Leu Gln Thr Lys Tyr
            115                 120

<210> SEQ ID NO 3
<211> LENGTH: 30
<212> TYPE: PRT
<213> ORGANISM: Viola spp.
<220> FEATURE:
<221> NAME/KEY: DOMAIN
<222> LOCATION: (0)...(0)
<223> OTHER INFORMATION: Mature cyclotide region

<400> SEQUENCE: 3

Lys Ile Pro Cys Gly Glu Ser Cys Val Tyr Ile Gly Cys Thr Leu Thr
 1               5                  10                  15

Ala Leu Ala Gly Cys Lys Cys Lys Asn Lys Val Cys Tyr Asn
            20                  25                  30

<210> SEQ ID NO 4
<211> LENGTH: 90
<212> TYPE: DNA
<213> ORGANISM: Viola spp.
<220> FEATURE:
<221> NAME/KEY: CDS
<222> LOCATION: (1)...(90)

<400> SEQUENCE: 4 aaa atc ccc tgc ggc gag agc tgc gtg tac att gga tgc aca ctc aca    48
Lys Ile Pro Cys Gly Glu Ser Cys Val Tyr Ile Gly Cys Thr Leu Thr
 1               5                  10                  15
```

```
gcc tta gct ggg tgc aaa tgc aag aac aaa gtt tgc tac aac          90
Ala Leu Ala Gly Cys Lys Cys Lys Asn Lys Val Cys Tyr Asn
             20                  25                  30

<210> SEQ ID NO 5
<211> LENGTH: 363
<212> TYPE: DNA
<213> ORGANISM: Artificial Sequence
<220> FEATURE:
<223> OTHER INFORMATION: Artificially created sequence optimized for
      expression in soybean (Glycine max)
<220> FEATURE:
<221> NAME/KEY: CDS
<222> LOCATION: (1)...(363)

<400> SEQUENCE: 5 atg gaa agt tac aag aag atg caa tta gtt ggc ttc gtc ttg ttg gct      48
Met Glu Ser Tyr Lys Lys Met Gln Leu Val Gly Phe Val Leu Leu Ala
 1               5                  10                  15 gct ttc gcc tta cca gca ttg gca tct tca ttc gag aag gat gtg atc      96
Ala Phe Ala Leu Pro Ala Leu Ala Ser Ser Phe Glu Lys Asp Val Ile
                 20                  25                  30 tct gct cat gca att cag gct gtt ctt gag aag aga gga ctc agt aaa     144
Ser Ala His Ala Ile Gln Ala Val Leu Glu Lys Arg Gly Leu Ser Lys
             35                  40                  45 cta gaa gac gat ccc gtg ctg agc gcc tta gcg tcc act aag acc atc     192
Leu Glu Asp Asp Pro Val Leu Ser Ala Leu Ala Ser Thr Lys Thr Ile
 50                  55                  60 ata tca aac cct gtc ata gag gaa gca tta ttg tca gga gca tct ctt     240
Ile Ser Asn Pro Val Ile Glu Glu Ala Leu Leu Ser Gly Ala Ser Leu
 65                  70                  75                  80 gaa gct ggt aac aaa att cca tgc ggc gaa agt tgc gta tac att ggg     288
Glu Ala Gly Asn Lys Ile Pro Cys Gly Glu Ser Cys Val Tyr Ile Gly
                 85                  90                  95 tgc aca ctc act gcc cta gct ggc tgt aag tgt aag aac aag gtt tgt     336
Cys Thr Leu Thr Ala Leu Ala Gly Cys Lys Cys Lys Asn Lys Val Cys
            100                 105                 110 tat aat agc ctg caa aca aaa tat tag                                 363
Tyr Asn Ser Leu Gln Thr Lys Tyr *
            115                 120

<210> SEQ ID NO 6
<211> LENGTH: 120
<212> TYPE: PRT
<213> ORGANISM: Artificial Sequence
<220> FEATURE:
<223> OTHER INFORMATION: Translation of artificially created
      soybean-optimized sequence of SEQ ID NO: 5
<220> FEATURE:
<221> NAME/KEY: DOMAIN
<222> LOCATION: (1)...(84)
<223> OTHER INFORMATION: N-terminal pro-peptide sequence
<220> FEATURE:
<221> NAME/KEY: DOMAIN
<222> LOCATION: (57)...(84)
<223> OTHER INFORMATION: N-terminal repeat fragment
<220> FEATURE:
<221> NAME/KEY: DOMAIN
<222> LOCATION: (85)...(114)
<223> OTHER INFORMATION: mature cyclotide sequence
<220> FEATURE:
<221> NAME/KEY: DOMAIN
<222> LOCATION: (115)...(120)
<223> OTHER INFORMATION: C-terminal fragment excised during processing

<400> SEQUENCE: 6
```

-continued

```
Met Glu Ser Tyr Lys Lys Met Gln Leu Val Gly Phe Val Leu Leu Ala
 1               5                  10                  15

Ala Phe Ala Leu Pro Ala Leu Ala Ser Ser Phe Glu Lys Asp Val Ile
            20                  25                  30

Ser Ala His Ala Ile Gln Ala Val Leu Glu Lys Arg Gly Leu Ser Lys
            35                  40                  45

Leu Glu Asp Asp Pro Val Leu Ser Ala Leu Ala Ser Thr Lys Thr Ile
     50                  55                  60

Ile Ser Asn Pro Val Ile Glu Glu Ala Leu Leu Ser Gly Ala Ser Leu
 65                  70                  75                  80

Glu Ala Gly Asn Lys Ile Pro Cys Gly Glu Ser Cys Val Tyr Ile Gly
            85                  90                  95

Cys Thr Leu Thr Ala Leu Ala Gly Cys Lys Cys Lys Asn Lys Val Cys
            100                 105                 110

Tyr Asn Ser Leu Gln Thr Lys Tyr
            115             120
```